US010624676B2

(12) United States Patent
Hawkins et al.

(10) Patent No.: US 10,624,676 B2
(45) Date of Patent: *Apr. 21, 2020

(54) SYSTEM AND METHOD FOR CERVICAL MIDLINE FIXATION

(71) Applicant: DePuy Synthes Products, Inc., Raynham, MA (US)

(72) Inventors: John Riley Hawkins, Cumberland, RI (US); Thomas J. Gamache, Westport, MA (US); Michael Sorrenti, Middleboro, MA (US); Alexander Grinberg, Auburndale, MA (US); Michael A. Fisher, Lawrenceville, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 71 days.

This patent is subject to a terminal disclaimer.

(21) Appl. No.: 15/861,270

(22) Filed: Jan. 3, 2018

(65) Prior Publication Data

US 2018/0140335 A1 May 24, 2018

Related U.S. Application Data

(60) Continuation of application No. 14/569,875, filed on Dec. 15, 2014, now Pat. No. 9,877,746, which is a
(Continued)

(51) Int. Cl.
*A61B 17/70* (2006.01)
*A61B 17/56* (2006.01)

(52) U.S. Cl.
CPC ........ *A61B 17/7032* (2013.01); *A61B 17/701* (2013.01); *A61B 17/7002* (2013.01);
(Continued)

(58) Field of Classification Search
CPC ............ A61B 17/7032; A61B 17/7034; A61B 17/7038; A61B 17/7037; A61B 17/7002;
(Continued)

(56) References Cited

U.S. PATENT DOCUMENTS

| 509,129 A | 11/1893 | Johnson |
|---|---|---|
| 2,551,636 A | 5/1951 | Ratigan |

(Continued)

FOREIGN PATENT DOCUMENTS

| WO | 98/35415 A1 | 8/1998 |
|---|---|---|
| WO | 2010/033567 A2 | 3/2010 |
| WO | 2011/056990 A2 | 5/2011 |

*Primary Examiner* — Ellen C Hammond
(74) *Attorney, Agent, or Firm* — Nutter McClennen & Fish LLP

(57) ABSTRACT

Devices and methods for enhancing the effectiveness of spinal stabilization, and particularly that of cervical spinal stabilization, are provided herein. More specifically, methods and systems are disclosed for effectively positioning occipital plates and spinal fixation assemblies within target vertebrae, while also reducing any associated patient trauma (e.g., muscle stripping, tissue damage, etc.). The systems and methods can utilize trans-lamina delivery of the spinal fixation assemblies to allow for the positioning of the fixation elements along the midline of the patient's spine.

18 Claims, 15 Drawing Sheets

Related U.S. Application Data division of application No. 13/222,913, filed on Aug. 31, 2011, now Pat. No. 8,940,023.

(52) U.S. Cl.
CPC ...... *A61B 17/7004* (2013.01); *A61B 17/7011* (2013.01); *A61B 17/7034* (2013.01); *A61B 17/7037* (2013.01); *A61B 17/7038* (2013.01); *A61B 2017/564* (2013.01)

(58) Field of Classification Search
CPC ................ A61B 17/7004; A61B 17/56; A61B 2017/564
See application file for complete search history.

(56) References Cited

U.S. PATENT DOCUMENTS

| | | | |
|---|---|---|---|
| 3,544,955 A | 12/1970 | Ruiz | |
| 5,330,473 A | 7/1994 | Howland | |
| 5,387,212 A | 2/1995 | Yuan et al. | |
| 5,437,669 A | 8/1995 | Yuan et al. | |
| 5,466,238 A | 11/1995 | Lin | |
| 5,562,663 A | 10/1996 | Wisnewski et al. | |
| 5,702,395 A | 12/1997 | Hopf | |
| 6,136,002 A | 10/2000 | Shih et al. | |
| 6,602,256 B1 | 8/2003 | Hayes | |
| 6,958,065 B2 | 10/2005 | Ueyama et al. | |
| 7,572,282 B2 | 8/2009 | Boomer et al. | |
| 7,678,137 B2 | 3/2010 | Butler et al. | |
| 8,052,726 B2 | 11/2011 | Nayet et al. | |
| 8,940,023 B2 | 1/2015 | Hawkins et al. | |
| 9,763,704 B2 | 9/2017 | Hawkins et al. | |
| 9,877,746 B2 | 1/2018 | Hawkins et al. | |
| 2004/0162558 A1 | 8/2004 | Hegde et al. | |
| 2005/0154391 A1 | 7/2005 | Doherty et al. | |
| 2005/0154393 A1 | 7/2005 | Doherty et al. | |
| 2005/0159750 A1 | 7/2005 | Doherty | |
| 2006/0206114 A1 | 9/2006 | Ensign et al. | |
| 2007/0233067 A1 | 10/2007 | Taylor | |
| 2007/0265621 A1 | 11/2007 | Matthis et al. | |
| 2008/0125781 A1* | 5/2008 | Hoffman | A61B 17/7055 606/331 |
| 2008/0125813 A1 | 5/2008 | Erickson et al. | |
| 2008/0228226 A1 | 9/2008 | Shamie | |
| 2008/0234681 A1 | 9/2008 | Baynham | |
| 2008/0281359 A1 | 11/2008 | Abdou | |
| 2009/0082812 A1 | 3/2009 | Lewis | |
| 2009/0125067 A1 | 5/2009 | Mazzuca et al. | |
| 2009/0216272 A1 | 8/2009 | Currier et al. | |
| 2009/0216278 A1 | 8/2009 | Song | |
| 2009/0287254 A1 | 11/2009 | Nayet et al. | |
| 2011/0301643 A1 | 12/2011 | Jahng | |
| 2013/0053886 A1 | 2/2013 | Hawkins et al. | |
| 2013/0053892 A1 | 2/2013 | Hawkins et al. | |
| 2013/0238033 A1* | 9/2013 | Black | A61B 17/7055 606/286 |
| 2015/0100092 A1 | 4/2015 | Hawkins et al. | |
| 2018/0344361 A1* | 12/2018 | Fiechter | A61B 17/7055 |

* cited by examiner

SYSTEM AND METHOD FOR CERVICAL MIDLINE FIXATION

CROSS-REFERENCE TO RELATED APPLICATIONS

This application is a continuation of U.S. application Ser. No. 14/569,875, filed on Dec. 15, 2014, now issued as U.S. Pat. No. 9,877,746, and entitled "System and Method for Cervical Midline Fixation." U.S. application Ser. No. 14/569,875 is a divisional of U.S. application Ser. No. 13/222,913, filed on Aug. 31, 2011, now issued as U.S. Pat. No. 8,940,023, and entitled "System and Method for Cervical Midline Fixation." The entire contents of these applications are expressly incorporated by reference herein.

FIELD OF USE

The present disclosure relates to devices and methods for use in various spinal fixation procedures, in particular to devices and methods for use in cervical stabilization procedures.

BACKGROUND

Stabilization of the spine is often required to correct for trauma, tumor, or degenerative pathologies. Current methods of treatment generally involve the use of a spinal fixation element, such as a relatively rigid fixation rod, that is coupled to adjacent vertebrae by attaching the fixation element to various anchoring devices, such as plates, hooks, bolts, wires, or screws. Spinal stabilization systems, which frequently include two fixation elements disposed on opposite sides of the midline of the spine, hold the vertebrae in a desired spatial relationship, until healing or spinal fusion has taken place, or for some longer period of time.

Due to the intricacies of working in the proximity of the spinal column, such stabilization procedures can result in significant trauma. For example, such procedures typically require that the anchoring devices be implanted into a lateral mass of a target vertebra. In light of this trajectory, significant amounts of muscle and tissue must be stripped from the treatment site due to the relatively large distance between the lateral mass entry point and the midline of the spinal column. Further, any slight miscalculation in the delivery trajectory can result in penetration of a distal portion of the anchoring device (e.g., a pointed tip) into the spinal canal, thereby causing significant injury. As a further disadvantage, the limited bone mass and/or bone density typically found in the lateral mass of a vertebra significantly limits the ability of the vertebra to effectively engage the anchoring devices.

Thus, there remains a need for methods and systems capable of securely positioning fixation assemblies within target vertebrae while also minimizing the risk of injury and associated patient trauma.

When such surgery is performed in the cervical spine, the fixation elements are typically molded according to the anatomy of the skull and the cervical spine, and attached to a fixation plate that is implanted in the occiput. Typically, the occipital plate (e.g., a T-shaped or Y-shaped plate) is positioned along the midline of a patient's occiput such that a single fixation plate can engage spinal fixation elements that run on either side of the midline.

Although each region of the spine presents unique clinical challenges, posterior fixation of the cervical spine is particularly challenging because the anatomy of the cervical spine makes it a technically difficult area to instrument. Specifically, several vital neural and vascular structures, including the vertebral arteries, nerve roots, and spinal cord must be avoided during surgery.

Accordingly, there remains a need for improved spinal fixation devices and methods of improving and/or optimizing cervical stabilization procedures.

SUMMARY

Devices and methods for enhancing the effectiveness of spinal stabilization, and particularly that of cervical spinal stabilization, are provided herein. More specifically, methods and systems are disclosed for effectively positioning occipital plates and spinal fixation assemblies within target vertebrae, while also reducing any associated patient trauma (e.g., muscle stripping, tissue damage, etc.). As described below, the systems and methods can utilize trans-lamina delivery of the spinal fixation assemblies to allow for the positioning of the fixation elements along the midline of the patient's spine.

Various aspects of an implantable assembly are provided herein. In a first aspect, an implantable assembly is provided which includes a plate having a bone contacting surface configured to be positioned on the occiput and an opposed surface for seating a spinal fixation element. The plate can have at least one opening extending through the bone contacting surface and the opposed surface for receiving an anchor element. Further, a pair of mating flanges can extend from the opposed surface and can be configured to receive a floating nut such that the floating nut and the opposed surface are configured to secure the spinal fixation element therebetween along a longitudinal axis of the plate. In one aspect, the longitudinal axis is configured to be positioned over a midline of the spine.

The bone contacting surface and the opposed surface can have a variety of configurations. For example, the opposed surface can include a groove for seating the spinal fixation element. In one aspect, the at least one opening can extend through the groove along the longitudinal axis of the plate. In another aspect, the at least one opening extends through the plate adjacent the groove, and can be, for example, disposed lateral to the longitudinal axis.

The floating nut can also have a variety of configurations. For example, the floating nut can have an inferior surface configured to seat the spinal fixation element. In one aspect, the floating nut can include lateral projections configured to slidably engage the flanges. By way of example, the lateral projections can dovetail with the flanges. The floating nut can also include a bore formed therethrough for receiving a locking element. The bore can, for example, extend through the floating nut substantially perpendicular to the longitudinal axis. In one aspect, the locking element can be configured to secure the floating nut to the spinal fixation element. In such an embodiment, engagement of the locking element with the spinal fixation element can prevent movement of the floating nut along the longitudinal axis relative to the plate. Further, in one aspect, the plate has at least two openings, and the floating nut can be positioned in a plane above a plane on which the two openings are disposed.

In another exemplary embodiment, a spinal fixation assembly is provided which includes a housing having an anterior base and a pair of arms extending posteriorly therefrom. The pair of arms define a slot therebetween that is configured to seat a spinal fixation element. The slot extends along a longitudinal axis of the housing and, in one aspect, is configured to be aligned with a midline of the spine. The housing can also have a central axis perpendicular to the longitudinal axis and extending through the base and the slot. An anchor-receiving opening, formed in at least one arm, extends between the slot and a bone contacting surface of the at least one arm adjacent the base. The at least one anchor-receiving opening is offset from the central axis and is configured such that at least one anchor member disposed therethrough extends inferiorly and laterally away from the housing at an acute angle relative to the central axis. For example, the anchor-receiving opening can be angled relative to the central axis to permit the anchor member to be implanted within the vertebra in a trans-lamina orientation.

In one aspect, the anchor-receiving opening can be defined by an internal surface of the housing that can, for example, be configured to engage a head of the at least one anchor member. In one aspect, the internal surface of the housing can be substantially spherical to allow for polyaxial movement of the at least one anchor member. The internal surface of the housing can also be configured to seat the head of the at least one anchor member offset from the central axis.

In one aspect, the base can also include a bone contacting surface adjacent the anchor-receiving opening. The bone contacting surfaces of the at least one arm and base can be configured to sit on the lamina.

In one embodiment, first and second arms of the housing can disposed on opposed sides of the central axis relative to one another. The second arm can include a window formed therethrough that is configured to provide access for a driver for manipulating an anchor member disposed through the anchor member opening in the first arm. In one embodiment, each of the first and second arms has an anchor-receiving opening. By way of example, a first anchor-receiving opening in the first arm can be configured to receive a first anchor member and a second anchor-receiving opening in the second arm can be configured to receive a second anchor member such that the first and second anchor members extend laterally away from the housing in different directions. In one aspect, the first and second anchor-receiving openings can be configured to receive the first and second anchors when the anchors are pre-installed in a vertebra.

In another aspect, a spinal fixation system is provided which includes a housing assembly, a spinal fixation element, and at least one anchor member. The housing assembly has a base and a pair of arms extending therefrom. The pair of arms define a slot therebetween that extends along a longitudinal axis of the housing and is configured to be aligned with a midline of the spine. The housing also includes a central axis that is perpendicular to the longitudinal axis and that extends through the base portion and the slot. As mentioned above, the system also includes a spinal fixation element that is configured to be disposed in the slot such that the spinal fixation element extends along a midline of the subject's spine. Further, the at least one anchor member is configured to be disposed through an anchor-receiving opening extending through at least one arm between the slot and a bone contacting surface of the at least one arm. The anchor member is offset from the central axis and extends away from the housing at an acute angle relative to the central axis.

In one embodiment, the spinal fixation element can be a rod. The rod can have various configurations, for example, of an irregular or rectangular cross-section. In one aspect, a fin can be coupled to the final fixation element. The fin can include one or more holes to which tissue can be attached. The anchor member can also have a variety of configurations. For example, in one embodiment, the anchor member can be a screw configured to be imbedded in a lamina. Alternatively, for example, the anchor member can be a hook configured to be hooked onto a lamina.

The system can also include a locking element configured to mate with the arms to secure the spinal fixation element within the slot. In one aspect, the inner surface of the arms can have threads for engaging the locking element.

Various aspects of a method of providing spinal stabilization are also disclosed herein. In one such aspect, the method includes fixing an occipital plate to the occiput of a subject with an anchor element and mounting a spinal fixation upon the occipital plate such that the spinal fixation element is positioned over a midline defined by the spinal column of a subject. The spinal fixation element can be secured to the occipital plate with a floating nut such that the spinal fixation element is positioned between the occipital plate and the floating nut. In one aspect, the floating nut can be slid along the spinal fixation element mounted on the occipital plate to position the floating nut between the spinal fixation element and a portion of the occipital plate.

The occipital plate can be fixed to the occiput in a variety of ways. By way of example, the occipital plate can be fixed to the occiput by inserting an anchor element into the occiput through at least one opening extending through the plate. In one embodiment, the at least one anchor element is inserted into the occiput on the midline. Further, the spinal fixation element can be positioned over the at least one anchor element. In another aspect, the at least one anchor element can be inserted into the occiput offset from the midline.

In another exemplary embodiment, a method of providing spinal stabilization is provided which includes positioning a first fixation assembly upon a first vertebra. The first fixation assembly includes a proximal housing having a base and a pair of arms and can be positioned such that a slot extending between the arms and along a longitudinal axis of the first fixation assembly is aligned with a midline of the spine. An anchor member, seated in the first fixation assembly, can extend away from the housing at an acute angle relative to a central axis that is generally perpendicular to the longitudinal axis. The method can also include positioning a second fixation assembly within a second vertebra such that a slot of the second fixation assembly is aligned with the slot of the first fixation assembly. A spinal fixation element can be positioned within the slots of the first and second fixation assemblies such that the spinal fixation element extends along a midline of the spine. Further, the spinal fixation element can be secured within the slots of the first and second fixation assemblies.

The first fixation assembly, which can be the same or different than the second fixation assembly, can be secured to the lamina in a trans-lamina orientation during the step of positioning a first fixation assembly upon a first vertebra. In such a method, the first fixation assembly can be secured to the first vertebra with a single anchor member. In one aspect, the anchor member can be seated in the fixation assembly before being secured to the lamina. In another embodiment, the first fixation assembly can be secured to the first vertebra with two anchor members implanted within the lamina on opposed sides of the midline. The anchor members can be seated in the fixation assembly after the anchor members are implanted in the lamina.

These and other aspects of the presently disclosed methods and systems are detailed below.

BRIEF DESCRIPTION OF THE DRAWINGS

The presently disclosed embodiments will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Devices, systems, and methods for optimizing various cervical stabilization procedures are described herein. The devices described herein can have a variety of configurations but are generally designed to allow a surgeon to position occipital plates and spinal fixation assemblies such that the spinal fixation element extends over a midline of patient's spine, thereby reducing the risk of trauma (e.g., muscle stripping, tissue damage, etc.) associated with prior posterior fixation procedures of the cervical spine. Additionally, the systems and methods described herein can also utilize trans-lamina delivery of the spinal fixation assemblies, thereby enabling more secure fixation through the use of larger (e.g., longer and/or wider) fixation assemblies relative to those of prior posterior fixation procedures, which engage the vertebra at locations more distant the midline (e.g., the lateral mass). As a further advantage, the delivery trajectory enabled by such trans-lamina delivery and positioning reduces the potential for inadvertent damage to the spine and/or surrounding areas because the assemblies can be angled away from the patient's spinal canal during delivery.

As indicated above, traditional spinal stabilization techniques typically require a first plurality of fixation assemblies (e.g., bone anchors coupled to a receiving head) engaged to a plurality of vertebrae along one side of the midline of a patient's spine, and a second plurality of fixation assemblies engaged to vertebrae along an opposite side of the midline. Once the fixation assemblies are secured to the vertebrae, a first rod is engaged to the first plurality of fixation assemblies, and a second rod is engaged to the second plurality of fixation assemblies. Next, a superior portion of each rod is engaged to an occipital plate such that the fixation elements extend from the cervical vertebrae to the occiput lateral to the midline. Generally, a single occipital plate spanning the midline is used to allow both the first and second rods to engage the same occipital plate.

Figure 1:
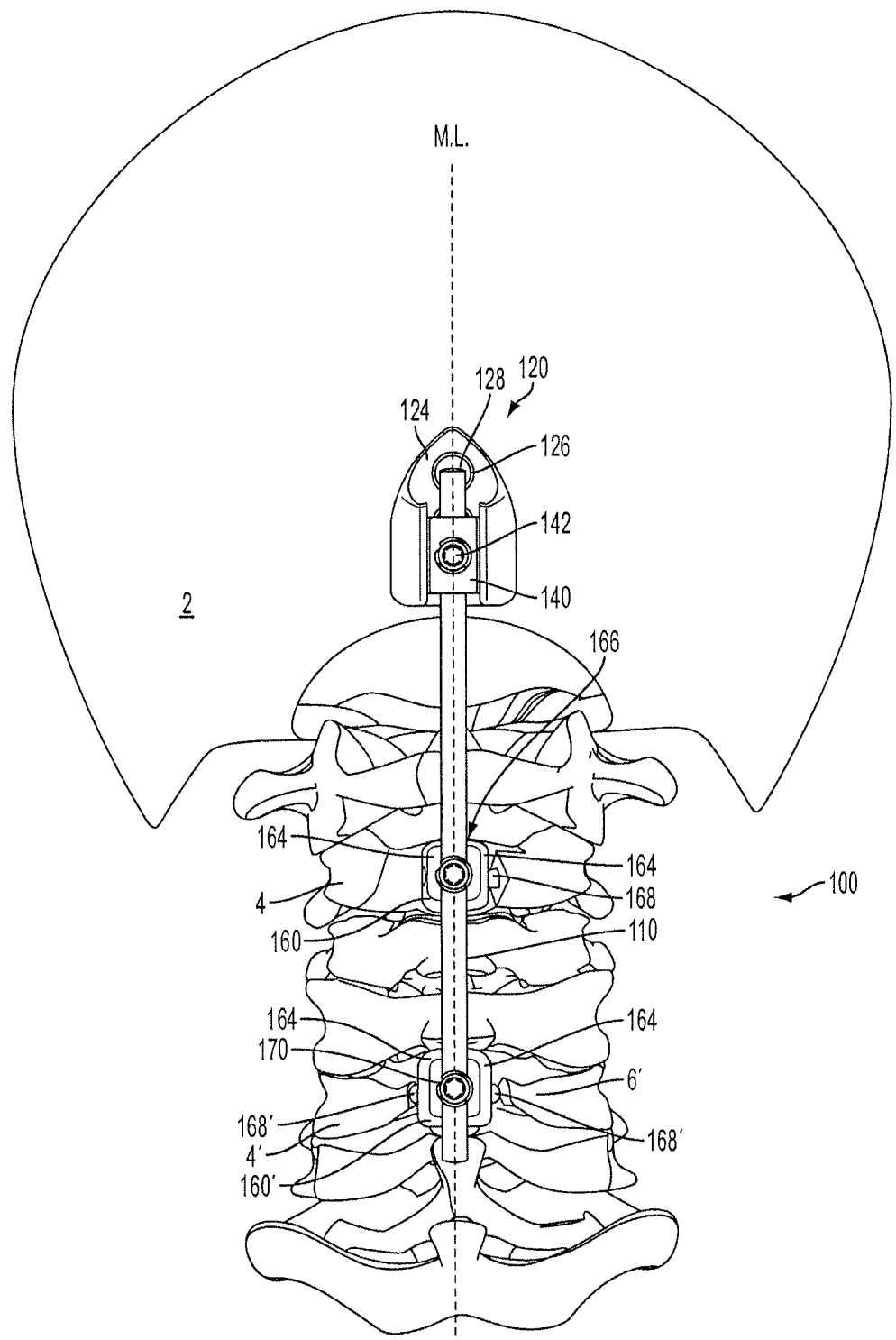
FIG. 1 is a posterior view of an exemplary embodiment of a spinal fixation system engaged at desired anatomical locations.

In contrast to unilateral or bilateral stabilization methods and systems in which the spinal fixation element(s) extend along the spine lateral to the midline of the patient's spine, FIG. 1 shows an exemplary embodiment of a cervical stabilization system 100 according to the teachings herein. The system 100 generally includes an occipital plate 120, first and second fixation assemblies 160, 160', and a spinal fixation element 110 extending therebetween. As shown, the occipital plate 120 can be engaged to the patient's occipital bone 2 on the midline (M.L.) of the patient's spine. As will be discussed in detail below, the occipital plate 120 can have a variety of configurations, but generally includes a bone contacting surface, an opposed surface 124 for seating the spinal fixation element 110, and at least one opening 126 extending therethrough. As shown in FIG. 1, the opening 126 can be configured to receive a bone screw 128 or any other type of suitable anchoring device so as to anchor the occipital plate 120 to the underlying occipital bone 2.

As shown in FIG. 1, the occipital plate 120 is generally configured to securely engage a spinal fixation element 110 disposed on the midline of a patient's spine. For example, the occipital plate 120 can be associated with a floating nut 140 that is configured to secure the spinal fixation element 110 between the floating nut 140 and the opposed surface 124 of the occipital plate 120 as will be discussed in detail below. A locking element 142, described further below, can be disposed within the floating nut 140 to securely couple the floating nut 140 to the spinal fixation element 110.

In addition to the occipital plate 120, the system 100 can also include a variety of spinal fixation assemblies that are generally configured to securely engage the vertebrae and provide a seat for the spinal fixation element 110 extending inferiorly from the occipital plate 120. As will be appreciated by a person skilled in the art, a variety of prior art spinal fixation assemblies modified in light of the teachings herein can be used in conjunction with the occipital plate 120 to position the spinal fixation element 110 on the midline of the spine.

Now with specific reference to the exemplary embodiments of spinal fixation assemblies 160, 160' depicted in FIG. 1, the spinal fixation assemblies 160, 160' include a housing having a pair of arms 164 extending posteriorly therefrom and disposed on opposed sides of the midline when implanted in the vertebrae. The arms 164 define a slot 166 therebetween that is configured to seat the spinal fixation element 110 along the midline of the spine. As will be discussed in detail below, the housing can have a central axis (perpendicular to the midline of FIG. 1) and an anchor-receiving opening offset from the central axis which extends through at least one of the arms 164. The anchor-receiving opening can be configured such that an anchor member disposed therethrough extends anteriorly and laterally away from the housing at an acute angle relative to the central axis. Thus, for example, the anchor member 168 extending from the superior fixation assembly 160 can be implanted in the lamina 6 of the vertebra 4 on one side of the midline, as shown in FIG. 1. Similarly, with respect to the inferior fixation assembly 160', the two anchor members 168' extend laterally away from the housing in different directions and are implanted in the laminae 6' of the vertebra 4' on opposite sides of the midline.

As will be discussed in detail below, various embodiments of the method for implanting the system 100 can include modifying or truncating various portions of the target vertebrae 4, 4' so as to further optimize the procedure and/or provide a desired clinical outcome (e.g., decompression to alleviate pressure on the spinal cord). Briefly, as shown in FIG. 1, the spinous process of the vertebra 4' has been removed, while the spinous process and one of the laminae (to the left in FIG. 1) has been removed from the vertebra 4. By removing these portions of the target vertebrae, the spinal fixation assemblies 160, 160' can access an optimal entry point of the vertebral bone and be positioned on the midline of the patient's spine.

As indicated above, the slots 166 of the spinal fixation assemblies 160, 160' can be aligned on the midline of the spine such that the slots 166 are configured to receive a spinal fixation element 110, such as a rod, extending from the occipital plate X along the midline. As shown in FIG. 1, the system 100 can further include a locking element 170 (e.g., set screw) that is configured to mate with the arms 164 of each of the spinal fixation assemblies 160, 160' to secure the spinal fixation element 110 within the slots 166.

One skilled in the art will appreciate that the occipital plate 120 and spinal fixation assemblies 160, 160' can be configured to receive a variety of fixation elements. Suitable spinal fixation elements for use with the present invention include, by way of non-limiting examples, rods, tethers, cables, plates, etc. The spinal fixation elements can have a variety of configurations, and, by way of non-limiting example, can be rigid, semi-rigid, bendable, flexible, etc. As will be appreciated by a person skilled in the art, the spinal fixation elements can include additional features which improve the integration of the system 100 within the patient's body. For example, in one embodiment, the spinal fixation element 110 can additionally include a fin to which soft tissue can be attached to promote integration and post-surgical recovery, as will be discussed in detail below.

In the exemplary embodiment illustrated in FIG. 1, the spinal fixation element 110 is an elongate rod. While the rod 110 can be substantially straight, in the illustrated embodiment, the rod 110 is bent or curved (not shown) to allow the rod to extend from the cervical vertebrae to the occipital plate 120 fixed on the occiput 2. The bend or curve can take any shape, but it can be preferable for the rod 110 to be complementary to a curve of the spine. Thus, the shape of the rod 110 can be substantially similar to a natural curve of the spine along the midline (M.L.). For example, the rod 110 can be curved to extend from the spinous process of one vertebra to the spinous process of an adjacent vertebra, while maintaining a close association with the contours of the spinal column therebetween. In some instances, the curve of the rod 110 can be pre-determined. In other instances, the rod 110 can include some flexibility to allow the rod 110 to be shaped in accord with its implant location. In even other instances, the rod 110 can be fully bendable so it can be formed into any desired shape along its length.

The rod 110 can also have a variety of cross-sections. For example, the rod 110 can have a circular cross-section. Alternatively, rods for use on the midline of the spine can also be shaped so as to provide increased torsional stability. For example, in one embodiment, the rod 110 can have an irregular and/or rectangular cross-section.

In addition to the various embodiments of the systems and devices for spinal stabilization described above, methods for providing spinal stabilization are also described herein. For example, with reference to FIG. 1, a method for cervical midline fixation can include fixing the occipital plate 120 to the occiput 2 of a subject, securing a first spinal fixation assembly 160 to a first vertebra 4, and securing a second fixation assembly 160' to a second vertebra 4'. In the depicted embodiment, the occipital plate 120 and first and second fixation assemblies 160, 160' are positioned so as to be aligned on the midline of the patient's spine. A spinal fixation element 110 can then be secured to the occipital plate 120 and the first and second fixation assemblies 160, 160' such that the spinal fixation element extends therebetween on the midline of the patient's spine.

Figure 2:
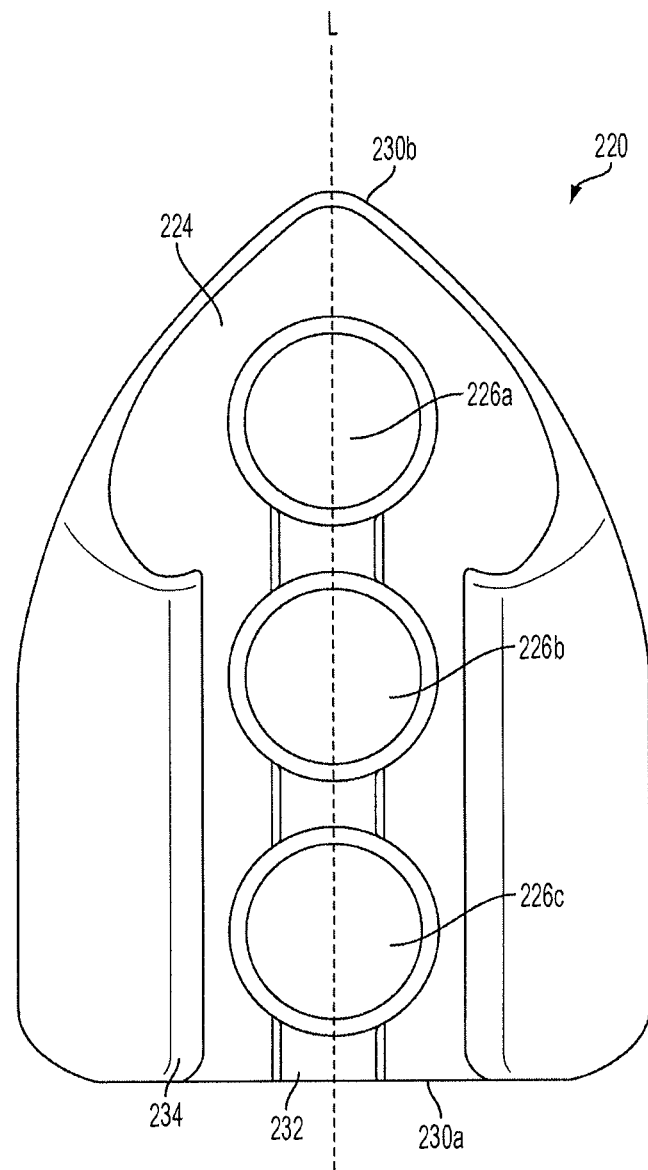
FIG. 2 is a posterior view of an exemplary embodiment of an occipital plate.
Figure 3:
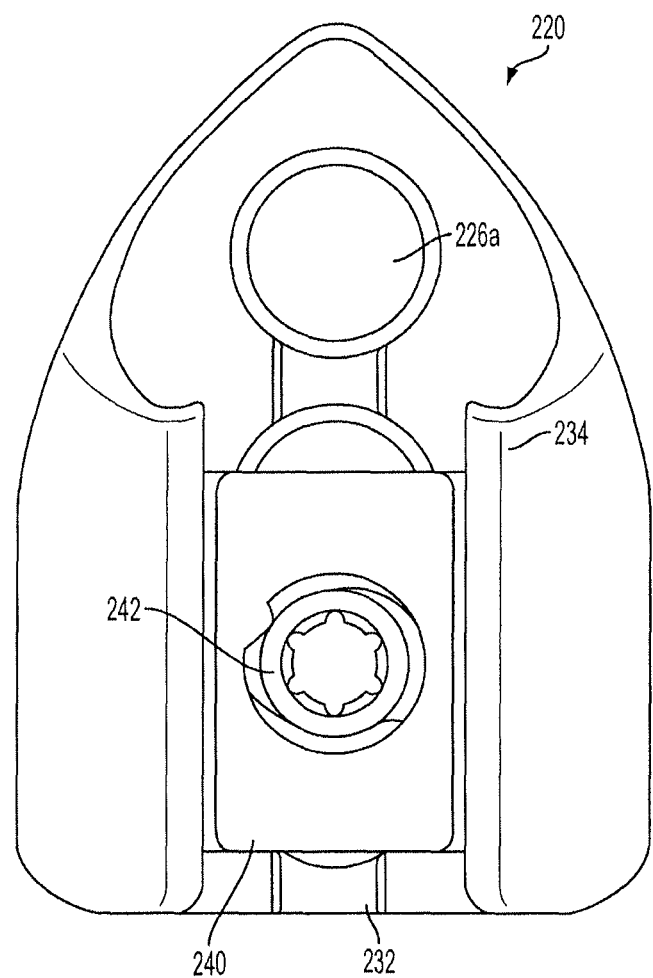
FIG. 3 is a posterior view of the occipital plate of FIG. 2, showing an exemplary embodiment of a floating nut engaged therewith.
Figure 4:
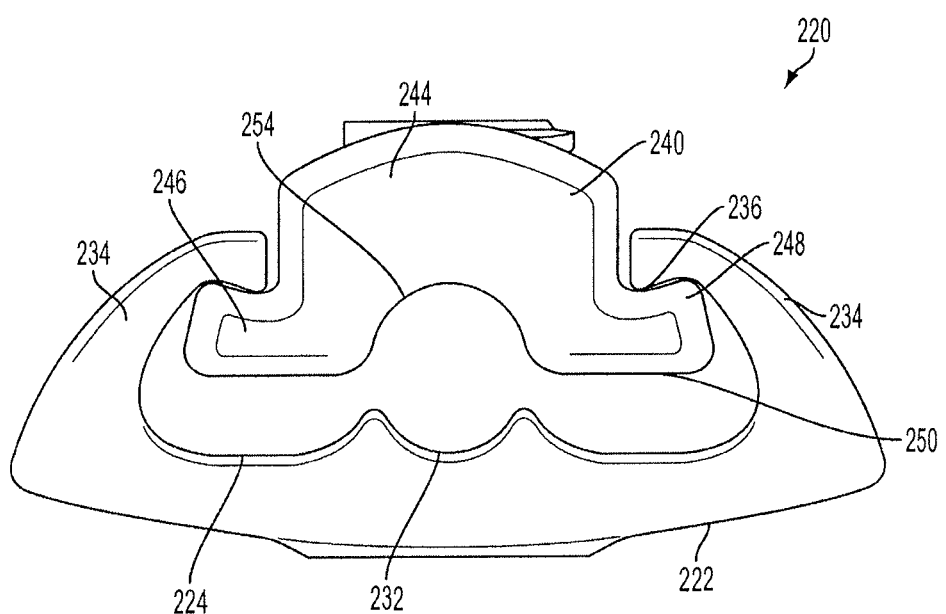
FIG. 4 is an inferior view of the occipital plate and floating nut of FIG. 3.

With reference now to FIGS. 2-4, one exemplary embodiment of an occipital plate 220 is shown in more detail. As indicated above, the occipital plate 220 can have a variety of configurations, but is generally configured to be fixed to a patient's occiput for securing a spinal fixation element thereto. As shown in FIG. 2, the occipital plate 220 can be in the form of a generally elongate member that defines a longitudinal axis (L) extending between inferior and superior ends 230a,b thereof. Though the occipital plate 220 can be fixed to any location of the occiput during surgery, in one embodiment, the longitudinal axis is configured to be aligned with a midline of the patient's spine when fixed to the occiput. The shape of the occipital plate 220 can vary, and will typically depend on the nature of the procedure and/or the patient's anatomy. For example, in one embodiment, the occipital plate can have a substantially constant width from the inferior end 230a to the superior end 230b. In the embodiment depicted in FIG. 2, however, the width of the occipital plate 220 tapers at the superior end 230b. Additionally, the inferior and superior ends 230a,b can be rounded (or even convex) so as to avoid the risk of damage during implantation.

As best shown in FIG. 4, the occipital plate 220 also includes a bone contacting surface 222 and an opposed surface 224 for seating a spinal fixation element. As will be appreciated by a person skilled in the art, the bone contacting surface 222 is configured to engage the occiput and can have a variety of configurations. For example, though the bone contacting surface 222 depicted in FIG. 4 presents a generally convex surface to the occiput, the bone-contacting surface 222 can be designed to have a shape that maximizes contact between the bone-contacting surface 222 and the occiput when implanted at a desired implantation site. Additionally, or in the alternative, the bone contacting surface 222 can include various surface features to aid engagement of the occipital plate 220 with the occiput. By way of example, the bone contacting surface 222 can include projections that are configured to pierce the occiput to help retain the occipital plate 220 at a desired implantation site until the occipital plate 220 is anchored thereto, as will be discussed in detail below.

Figure 6:
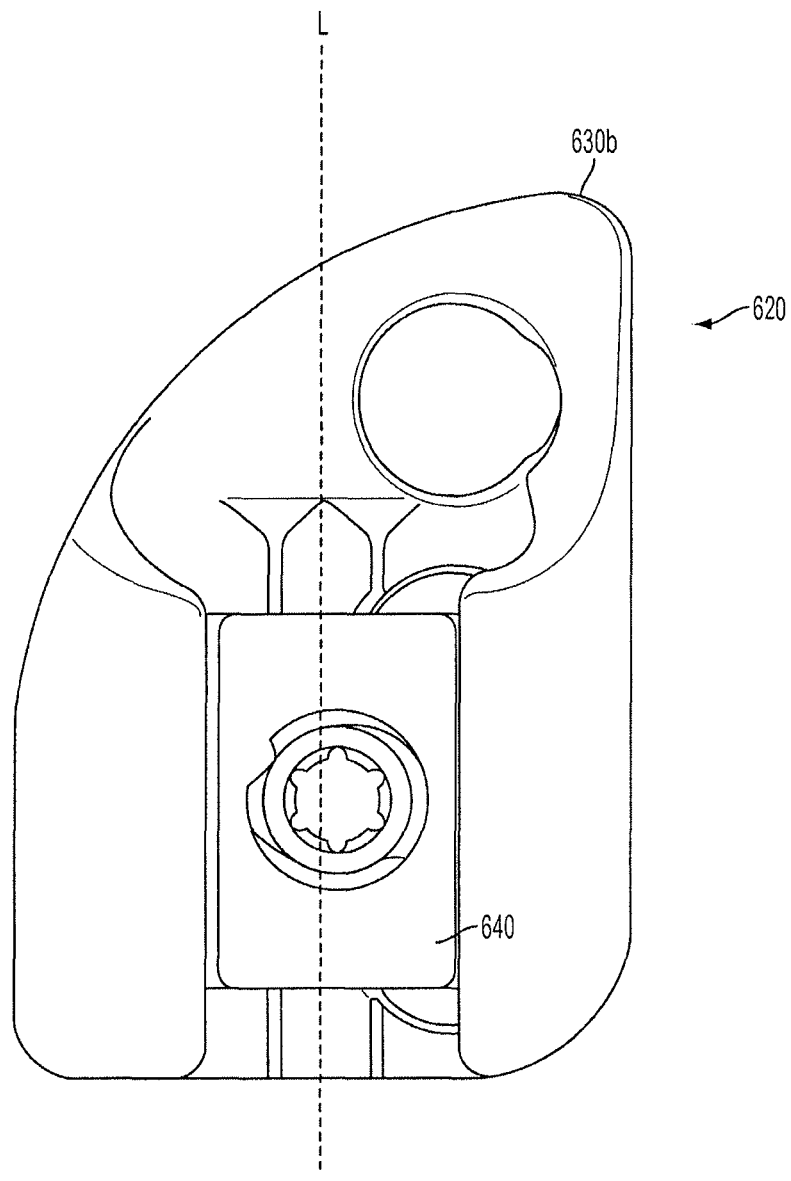
FIG. 6 is a posterior view of another exemplary embodiment of an occipital plate, showing a floating nut engaged therewith.

Further, with reference now to FIG. 6, in one exemplary embodiment of an occipital plate 620, the occipital plate 620 need not be symmetrical about the longitudinal axis (L). For example, as shown in FIG. 6, the superior most end 630b of the occipital plate 620 can be offset from the longitudinal axis, thereby allowing a surgeon to select an occipital plate having a shape that best conforms to the desired implantation site. By way of example, a surgeon could opt to use the occipital plate 620 rather than the occipital plate 220 depicted in FIGS. 2-4 to ensure close contact between the bone contacting surface 622 and the occiput and/or to avoid a protuberance or other such surface feature of the occiput that would prevent the superior end 230b of the occipital plate 220 from laying flush against the bone surface on the midline.

Figure 7:
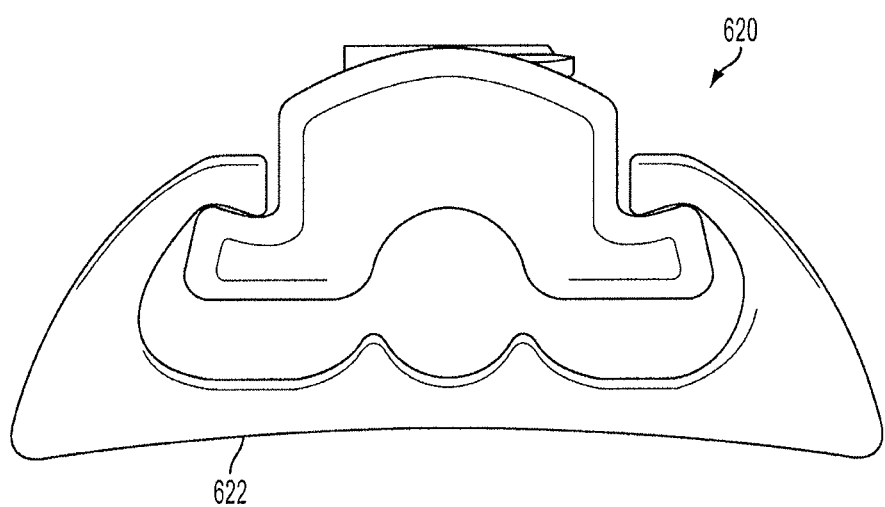
FIG. 7 is an anterior view of the occipital plate and floating nut of FIG. 6.

As noted above, the bone-contacting surface can also be contoured so as to substantially conform to a patient's particular anatomical features at the desired implantation site. By way of example and with reference now to FIG. 7, the bone-contacting surface 622 of the occipital plate 620 can present a substantially concave surface to the occiput to accommodate surface features of the occiput (e.g., the median nuchal crest).

Although the occipital plates described herein can be generally rigid and/or planar, it should be appreciated that the occipital plate 220 can be configured to allow a surgeon to adapt the bone-contacting surface 222 to the target implantation site. For example, the occipital plate 220 can be formed of a flexible or malleable material thereby allowing the occipital plate 220 to conform to the target implantation site. In other embodiments, the occipital plate 220 can include one or more bend zones formed therein to allow the occipital plate 220 to conform the plate to a surface of the target anatomical location. By way of non-limiting example, the bend zones can be formed from channels that partially extend between the bone-contacting surface 222 and the opposed surface 224. Those skilled in the art will appreciate that a variety of other techniques can be used to provide bendable movement of one or more portions of the occipital plate 220.

Again referring to the exemplary embodiment depicted in FIGS. 2-4, the opposed surface 224 of the occipital plate 220 is generally configured to seat a spinal fixation element and can also have a variety of configurations. By way of example, the opposed surface 224 includes a groove 232 that is configured to seat a spinal fixation element therein. The groove 232 extends superiorly along the opposed surface 224 from the interior end 230a and can be shaped so as to substantially correspond to the cross-section of the spinal fixation element. Though the groove 232 depicted in FIG. 4 includes a semi-circular surface configured to match the outer surface of a spinal fixation element having a circular cross-section, the groove 232 can alternatively be shaped so as to match the outer surface of a spinal fixation element having other cross-sectional shapes. That is, the shape of the groove 232 can be selected to accommodate a spinal fixation element having, for example, an irregular or rectangular cross-section.

As noted above, the occipital plate 220 can also include any number (e.g., 1, 2, 3, 4, 5, etc.) of openings configured to receive a corresponding number of bone screws (not shown) or any other type of suitable anchoring devices for anchoring the occipital plate 220 to the underlying bone. For example, in the exemplary embodiment of FIGS. 2-4, the occipital plate 220 includes three such openings 226a-c. As will be appreciated by those skilled in the art, the openings 226a-c can be of any shape (e.g., circular, oval, etc.) and/or diameter capable of securely receiving a bone screw or other suitable anchoring device. Additionally, each of the openings 226a-c can be substantially similar in shape (as shown) or they can each have a distinct shape and/or diameter. In one embodiment, the openings can have a keyhole configuration to enable a suitable anchoring device (e.g., a threaded post) to be implanted within the occiput prior to positioning the occipital plate 220 on the occiput. In this manner, the occipital plate 220 (with or without the fixation element and floating nut engaged therewith) can be inserted over a portion (e.g., head) of the pre-implanted anchoring device and manipulated to securely engage the keyhole opening(s) to fix the occipital plate 220 to the occiput.

Figure 8:
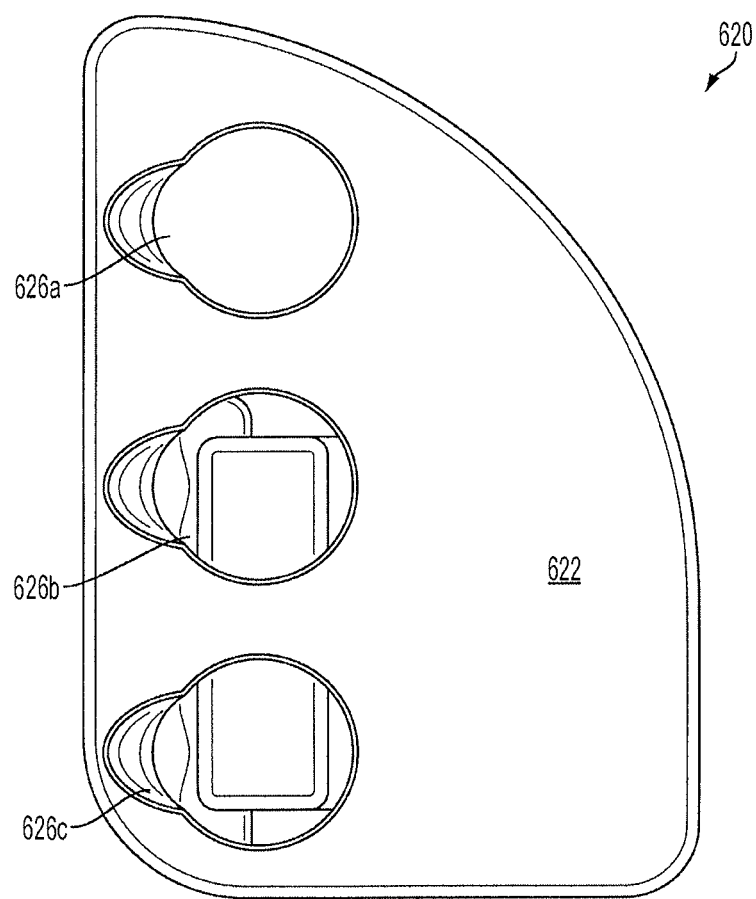
FIG. 8 is an anterior view of the occipital plate and floating nut of FIG. 6.

With reference now to FIG. 8, in one exemplary embodiment of an occipital plate 620, the openings 626a-c can be configured so as to promote an angular displacement of anchor members disposed therethrough. That is, the openings 626a-c can be configured such that an anchor member disposed therethrough is not directed substantially perpendicular to the plane of the bone-contacting surface 622. For example, as shown in FIG. 8, the lateral edge of openings 626a-c can be beveled to enable an anchor member to extend laterally away from the occipital plate 620. As will be appreciated by a person skilled in the art, the shape of the openings 626a-c can be designed such that a bone screw disposed through the openings 626a-c is directed to an area of the occiput having sufficient bone density for anchoring the occipital plate thereto.

Further, the alignment and/or positioning of the openings 226a-c can also be optimized to conform to the desired anatomical location. For example, the location of the openings 226a-c can be selected such that a bone screw disposed through the openings 226a-c is directed to an area of the occiput having sufficient bone density for anchoring the occipital plate thereto. As shown in FIG. 2, for example, each of the openings 226a-c extend through the groove 232 and are substantially aligned with one another along the longitudinal axis (L) of the occipital plate 220. In other embodiments, however, at least one of the openings 226a-c can be offset (e.g., staggered) relative to the others.

The openings 226a-c, however, need not be aligned with the central axis. With reference now to FIG. 6, in one exemplary embodiment of an occipital plate 620, each of the openings 626a-c instead extend through the bone-contacting surface 622 and the opposed surface 624 offset from (e.g., lateral to) the longitudinal axis (L) of the occipital plate 620. Accordingly, the openings 626a-c extend through the occipital plate 620 adjacent the groove 632 rather than through the groove 232 as depicted in FIGS. 2-4. Thus, though the longitudinal axis and the groove 632 of the occipital plate 620 can be aligned with the midline of the patient's spine, the offset openings 626a-c can enable anchors to be implanted in the occiput at locations lateral to the midline, for example, to avoid diseased bone or bone of insufficient thickness or density.

As indicated above, the occipital plate is configured to securely engage a spinal fixation element disposed on the midline of a patient's spine. It should be appreciated that a variety of engagement mechanisms known in the art can be used to secure a spinal fixation element to the occipital plate. By way of example, the occipital plate 220 can be configured to receive a set screw (e.g., a dual innie) effective to secure a spinal fixation element to the plate. With specific reference now to FIGS. 2-4, in an exemplary embodiment, the occipital plate 220 includes a pair of flanges 234 that extends from the opposed surface 224. The opposed flanges 234 can have a variety of configurations, but generally are configured to cooperate with a floating nut 240 to secure the spinal fixation element between the floating nut 240 and the opposed surface 224 of the occipital plate 220.

As best viewed in FIG. 4, the flanges 234 extend from the lateral edges of the opposed surface 224 posteriorly and centrally toward the longitudinal axis (L) of the occipital plate 220, thereby forming a cavity between an inner surface of the flanges 234 and the opposed surface 224. As shown, the terminal ends of the flanges 234 extend substantially parallel to the opposed surface 224 and include a protrusion 236 which extends toward the opposed surface 224.

The floating nut 240 can be configured to engage the flanges 234 of the occipital plate 220 and can also have a variety of configurations. In the exemplary embodiment depicted in FIG. 4, the floating nut 240 can include a central portion 244 and lateral projections 246 which extend laterally away from the central portion 244. The lateral projections 246 can additionally include protrusions 248 that are configured to mate with and slidably engage the protrusions 236 of the flanges 234 in a dove-tailed manner. In some embodiments, the lateral projections 246 can additionally include engaging teeth (not shown) which can be configured to engage reciprocal features formed on the flanges 234 of the occipital plate 220. In this manner, the engaging teeth and reciprocal features can act as a ratchet to inhibit disengagement and/or removal of the floating nut 240 from the occipital plate 220.

The central portion 244 of the floating nut 240 can also include a posterior surface 250 and an anterior surface 252, at least a portion of which is configured to seat a spinal fixation element. By way of example, the anterior surface 252 includes a channel 254 that is configured to be disposed in facing relationship with the groove 232 formed in the opposed surface 224 when the floating nut 240 engages the flanges 234. As discussed above, though the channel 254 is depicted as having a semi-circular surface that is configured to seat a spinal fixation element having a circular cross-section, the channel 254 can be shaped so as to correspond to spinal fixation element having other cross-sectional shapes (e.g., rectangular, irregular).

Figure 5:
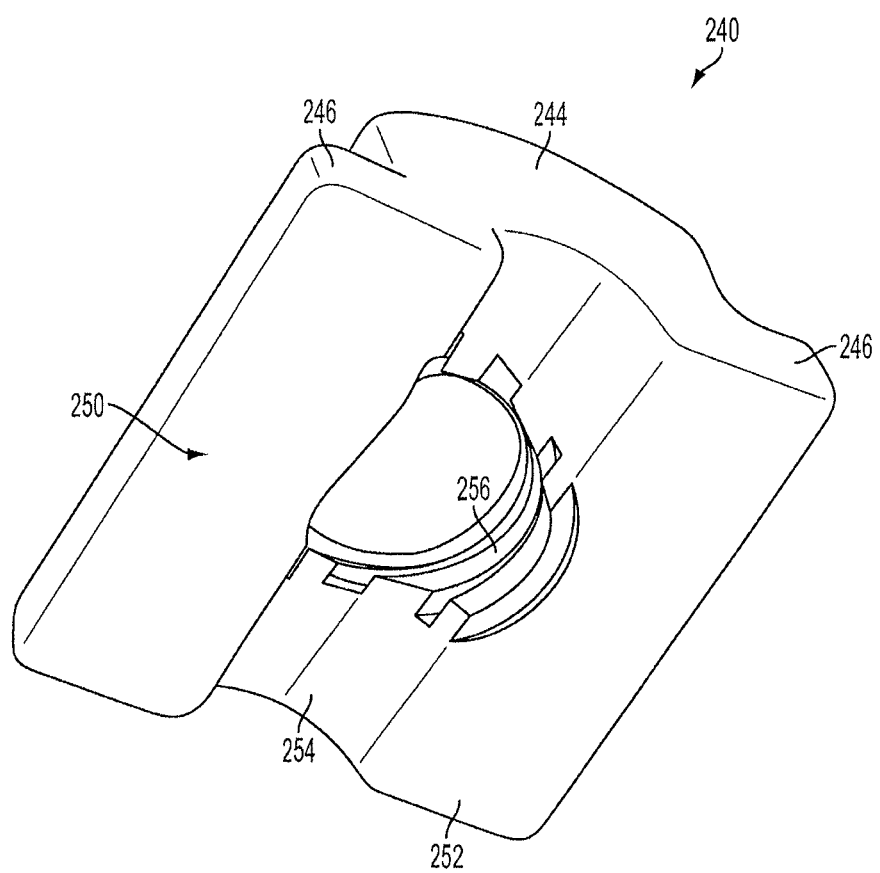
FIG. 5 is a perspective view of the floating nut of FIG. 3.

As best shown in FIG. 5, the central portion 244 of the floating nut 240 can also include a bore 256 extending from the posterior surface 250 to the anterior surface 252. The bore 256 can have a variety of configurations, but generally is configured to allow a locking element 242 disposed therein to engage a spinal fixation element disposed in the channel 254 formed in the anterior surface 252. By way of example, the locking element 242 can be advanced (e.g., threaded) within the bore 256 to secure the floating nut 240 to the spinal fixation element. Accordingly, through the cooperation of the lateral projections 246 of the floating nut 240 with the flanges 234 of the occipital plate 240 and the engagement of the spinal fixation element with the floating nut 240, the floating nut 240 can be positioned in a plane above a plane of the opposed surface 224 such that the spinal fixation element is securely engaged between the floating nut 240 and the opposed surface 224 of the occipital plate 220. Movement of the floating nut 240 (and the spinal fixation element) away from the opposed surface 224 and/or movement of the floating nut 224 along the central axis (C) of the occipital plate 220 can thus be prevented.

In use, the occipital plate 220 depicted in FIGS. 2-5 can be fixed to the occiput with one or more anchor elements. Further, a spinal fixation element can be mounted upon the occipital plate 220 (e.g., seated in the groove 232) such that the spinal fixation element is positioned over a midline defined by the spinal column of the subject, and over any anchor members that are positioned along the longitudinal axis (L) of the occipital plate. The spinal fixation element can then be secured to the occipital plate 220 with the floating nut 240 such that the spinal fixation element is positioned between the occipital plate 220 and the floating nut 240.

As discussed above, the occipital plate 220 can be fixed to the occiput using various anchor members known in the art. By way of example, the occipital plate 220 can be fixed to the occiput by inserting an anchor element through at least one of the openings 226a-c extending through the bone contacting surface 222 and the opposed surface 224 of the occipital plate 220. Further, the anchor elements can be inserted into the occiput at a variety of locations, depending, for example, on the patient's anatomy. By way of example, the surgeon can fix an occipital plate 220 to the occiput on the midline via one or more anchor members, and the spinal fixation element can be positioned on the occipital plate 220 thereover. Alternatively, an anchor element can be inserted through the occipital plate 220 offset from the midline, for example, to avoid diseased bone or a particularly prominent feature of the patient's occiput.

The method of implanting the occipital plate 220 can also include sliding the floating nut 240 along the spinal fixation element mounted on the occipital plate 220 to position the floating nut 240 between the spinal fixation element and a portion of the occipital plate 220. For example, the spinal fixation element can be seated within the channel 254 such that the floating nut 240 can be slid therealong such that the lateral projections 246 of the floating nut 240 engage the flanges 234 of the occipital plate 220.

As indicated above, spinal fixation assemblies for use in the systems and methods described herein can have a variety of configurations but are generally configured to secure a spinal fixation element on the midline of a patient's spine. Referring now to FIGS. 9-15, exemplary embodiments of a spinal fixation assembly are shown in further detail. As will be appreciated by a person skilled in the art, a variety of prior art spinal fixation assemblies can be modified in light of the teachings herein for use in conjunction with other portions of the system 100 of FIG. 1 for positioning the spinal fixation elements 110 on the midline of the spine.

Figure 9:
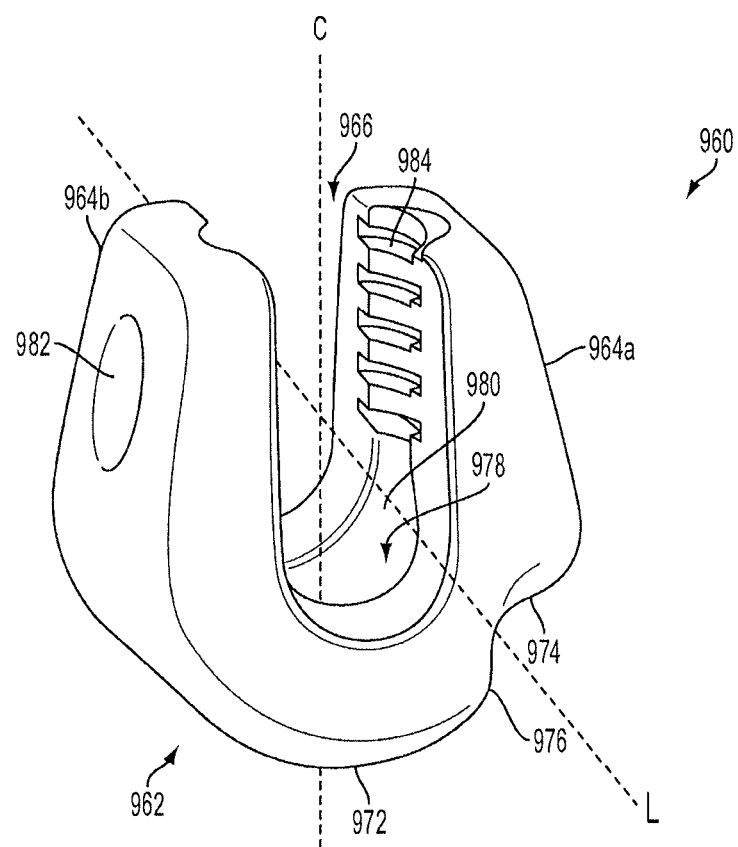
FIG. 9 is a perspective view of an exemplary embodiment of a housing of a spinal fixation assembly.
Figure 10:
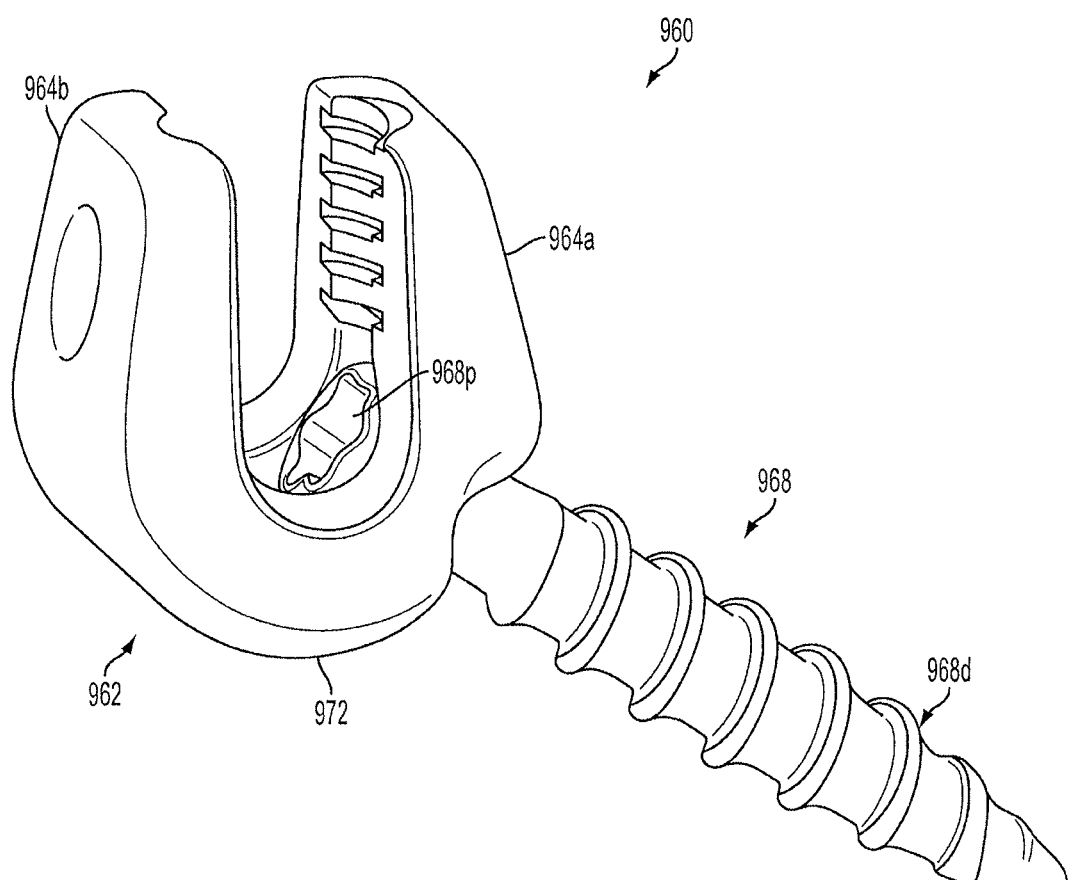
FIG. 10 is a perspective view of the housing of FIG. 9 having a single anchor member disposed therein.
Figure 11:
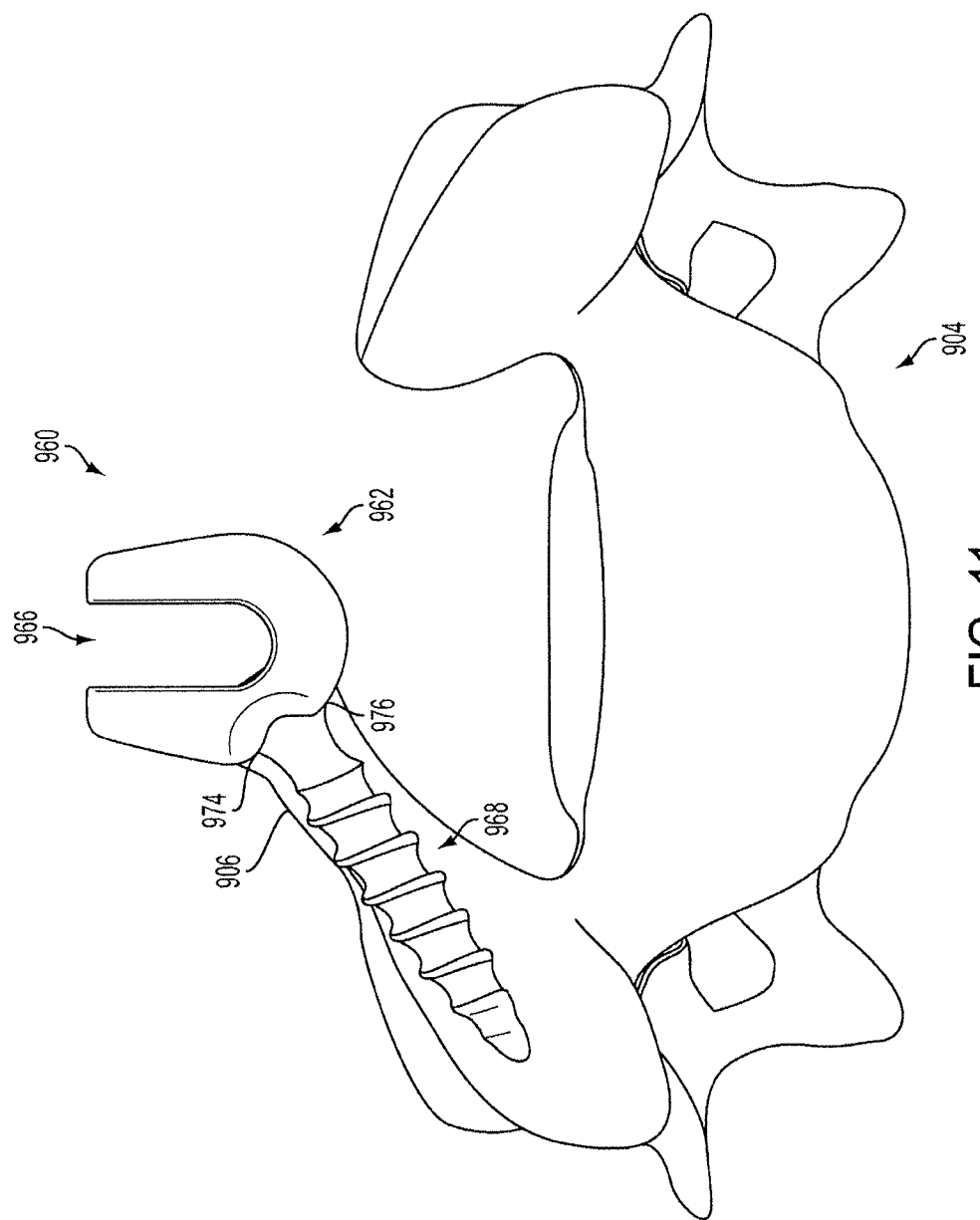
FIG. 11 is a superior view of the housing of FIG. 9 having a single anchor member positioned within the lamina of a vertebra, wherein portions of the vertebra have been truncated prior to securing the assembly thereto.

With specific reference to FIGS. 9-11, one embodiment of a spinal fixation assembly 960 is shown. The spinal fixation assembly 960 includes a housing 962 that is configured to seat a spinal fixation element (e.g., a rod). The housing 962 can be configured in virtually any manner capable of receiving and securing the spinal fixation element therein. In the exemplary embodiment depicted in FIG. 9, the housing 962 includes a base portion 972 and a pair of arms 964a,b extending posteriorly therefrom. The arms 964a,b can have a variety of configurations but generally define a slot 966 (e.g., a U-shaped opening) which extends along the longitudinal axis (L) of the housing. Thus, as described otherwise herein, the housing 962 can be positioned relative to the spine such that the arms 964a,b are disposed on opposed sides of the midline and the slot 966 and longitudinal axis (L) are aligned with the midline of the spine. A central axis (C) can also be defined by the housing 962, the central axis (C) being perpendicular to the longitudinal axis (L) and extending through the base 972 and the slot 966.

As will be discussed in more detail below with reference to FIG. 11, at least a portion of the arm 964a can be configured to contact bone. For example, the arm 964a can include a bone-contacting surface 974 having a profile configured to correspond to the surface of a lamina 906 that has been prepared for implantation of the spinal fixation assembly 960. Accordingly, when an anchor member 968 is fully implanted in the lamina 906, the bone-contacting surface 974 can sit on the lamina 906 to stabilize the spinal fixation assembly 960 relative thereto. Similarly, the base 972 can include a bone-contacting surface 976 adjacent an anchor-receiving opening 978 that can also be configured to sit on the lamina 906 when an anchor member 960 is fully implanted therein.

The housing 962 can also seat at least one bone anchor member that is configured to securely engage a vertebra. In the embodiment depicted in FIG. 10, the housing 962 is configured to receive a single anchor member 968. Any suitable type of anchoring device (e.g., plates, hooks, bolts, wires, screws, etc.) can be used to anchor the housing 962 to the vertebra. By way of example, the housing 962 can be configured to receive a hook that securely engages a portion (e.g., lamina(e), spinous process) of a vertebra, without necessarily penetrating the vertebral bone. As shown in FIG. 10, the anchor member can be a bone screw 168 having a proximal head 968p and a threaded distal shank 968d configured to be implanted within a portion of the vertebra. While the bone anchor 968 can have a wide range of sizes and/or shapes, as indicated above, an advantage of translamina delivery can be the ability to utilize larger bone anchors 968 as compared to the traditional lateral mass approach.

As will be appreciated by a person skilled in the art, the bone anchor 968 can be securely seated within the housing using a variety of mechanisms. For example, in the depicted embodiment, the housing 962 includes an anchor-receiving opening 978 formed in one of the arms 964a. The anchor-receiving opening 978 can be disposed through various portions of the arm 964a, but in the embodiment shown in FIG. 9, the anchor-receiving opening 978 extends between the slot 966 and a bone-contacting surface 974 of the arm 964a adjacent the base 972 such that the anchor-receiving opening 978 is offset from the central axis (C). In the embodiment depicted in FIG. 10, the anchor screw 968 is seated within the housing 962 such that the distal shank 968d of the anchor screw 968 extends through the anchor-receiving opening 978 inferiorly and laterally away from the housing 962.

Additionally, the anchor-receiving opening 978 can also be configured such that an anchor member is retained in the housing 962. By way of example, the anchor-receiving opening 978 can have a minimum diameter that is greater than the maximum diameter of the shaft 968d and less than a maximum diameter of the head 968p such that the anchor receiving opening 978 can be effective to retain the head 968p of the anchor member 968 within the housing 962 while allowing the shaft 968d to extend therefrom.

The anchor-receiving opening 978 can also be configured such that the anchor member extends therefrom with either a fixed or adjustable orientation relative to the housing 962. By way of example, in one embodiment, the internal surface 980 of the housing 962 which defines the anchor-receiving opening 978 can be disposed at a selected angle relative to the central axis (C) and can be sized or configured such that the distal shaft 968d of the anchor member 968 necessarily extends through the anchor-receiving opening 978 and from the housing 962 at the selected angle. Alternatively, the internal surface 980 of the housing 962 can be configured to seat the proximal head 968p of an anchor member 968 so as to allow the angular orientation of the distal anchor 968d to be adjusted relative to the housing 962. For example, as shown in FIG. 10, the internal surface 980 of the housing 962 can be configured to allow for polyaxial movement of the anchor member 968 engaged therewith. By way of example, the internal surface 980 of the housing 962 be substantially spherical so as to correspond with a spherical head 968p of the anchor member 968, such that the head 968p can rotate relative to the housing 962 as in a ball-and-socket joint. In this manner, the angle at which the anchor member 968 extends from the housing can be altered based on the particular anatomy at a desired implantation site.

In one embodiment, the arms 964a,b can additionally include features that provide access to the slot 966 and/or the anchor-receiving opening 978. For example, as shown in FIGS. 9 and 10, the arm 964b disposed on the opposed side of the central axis (C) relative to the arm 964a can include a window 982 formed therethrough. The window 982 can extend between a lateral surface of the arm 964b and the slot 966 and can be configured to provide access to various instruments (e.g., driver, drill, etc.). By way of example, the window 982 can provide access for modifying a bone surface through the anchor-receiving opening 978 (e.g., forming a bore at a desired implantation site) or for manipulating an anchor member 968 disposed through the anchor-receiving opening 978.

As will be appreciated by a person skilled in the art, the housing 962 can also include an engagement mechanism for securing a spinal fixation element within the slot 966. As shown in FIG. 9, for example, the arms 964a,b can include internal threads 984 configured to receive a closure mechanism (e.g., a set screw) to thereby secure a spinal fixation element disposed within the slot 966 to the housing 962.

Referring now to FIG. 12-15, another embodiment of a spinal fixation assembly 1260 is shown. Similar to the spinal fixation assembly 960 described above with reference to FIGS. 9-11, the spinal fixation assembly 1260 includes a housing 1262 that is configured to seat a spinal fixation element 1210 within a slot 1266 formed between a pair of arms 1264a,b which extend from a base 1272. The spinal fixation assembly 1260 depicted in FIGS. 12-14 differs however, in that the housing 1262 is configured to seat two anchor members 1268a,b offset from the central axis (C). As best viewed in FIG. 14, the two anchor members 1268a,b can extend laterally away from the housing 1262 in different directions. Such a configuration, for example, allows the housing 1262 to be positioned on the midline of a patient's spine and to be coupled to both laminae of a vertebra.

Figure 12:
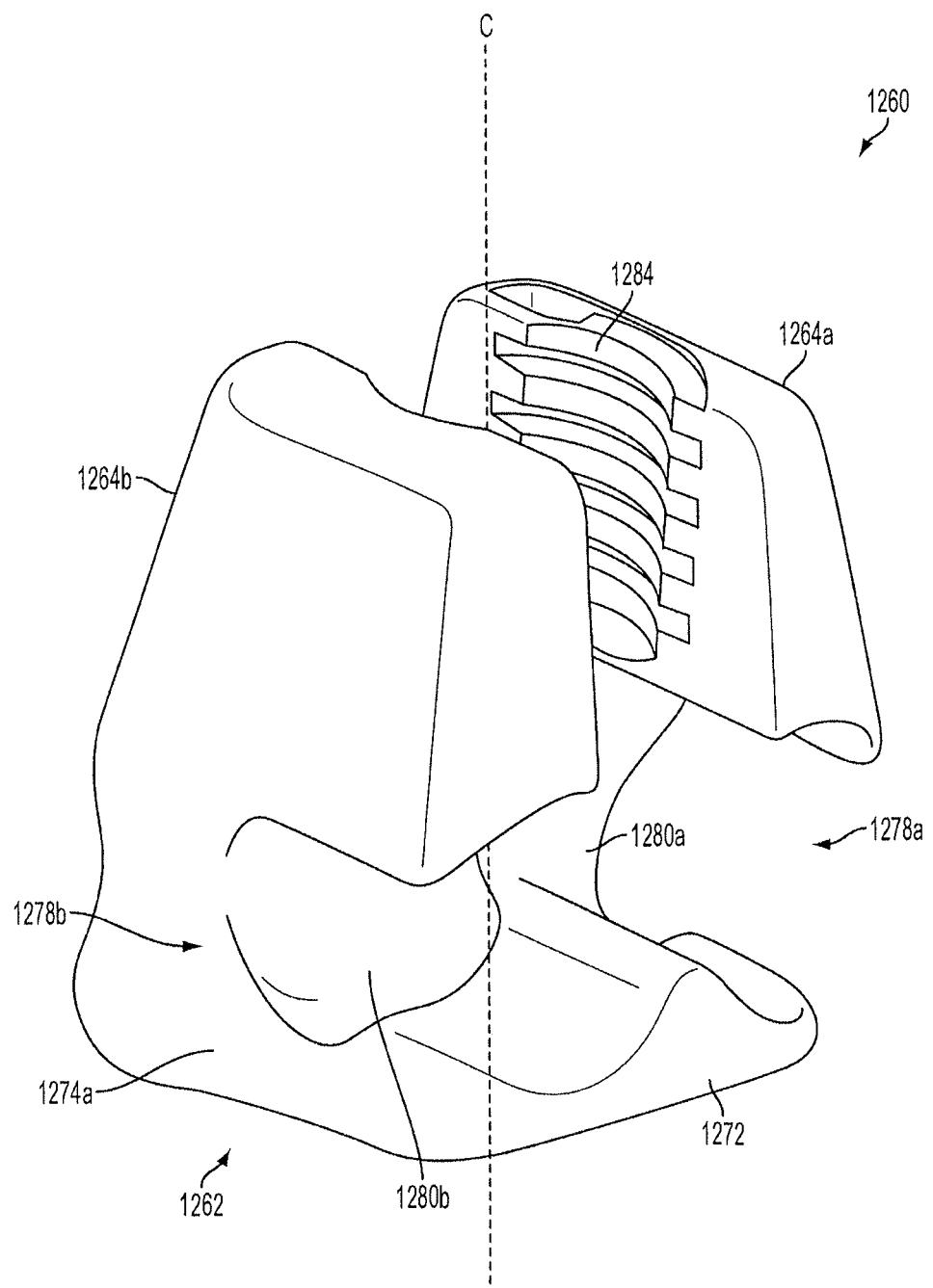
FIG. 12 is a perspective view of another exemplary embodiment of a housing of a spinal fixation assembly.
Figure 13:
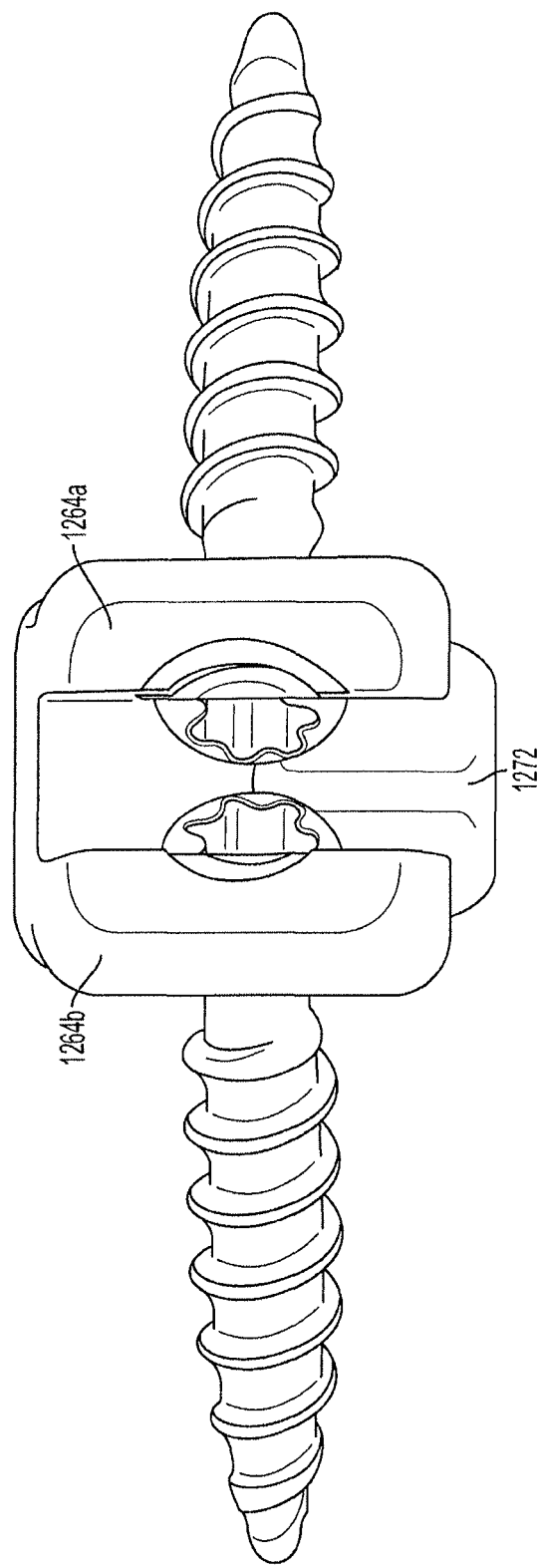
FIG. 13 is a posterior view of the housing of FIG. 12 having two anchor members disposed therein.

As best viewed in FIG. 12, the housing 1262 includes two anchor-receiving openings 1278a,b formed in the arms 1264a,b and extending between the slot 1266 and bone-contacting surfaces 1274a,b. Unlike the spinal fixation assembly 960 depicted in FIG. 9, however, the internal surface 1280a,b of the housing 1262 which defines the anchor-receiving openings 1278a,b does not fully enclose the anchor-receiving openings 1278a,b. That is, the arms 1264a,b extend from only a single "closed" side of the housing 1262. As will be discussed in detail below, the "open" side of the housing 1262 therefore can allow the housing 1262 to receive proximal heads 1268p of bone anchors 1268 that have been pre-installed in vertebral bone.

Further, though the arms 1264a,b of the spinal fixation assembly 1260 are shown without a window 982 as depicted in FIGS. 9-11, one of skill in the art will understand that the arms 1264a,b can additionally include windows to provide access to the heads 1268p of the bone anchors 1268a,b seated within the anchor-receiving openings 1278a,b.

Figure 14:
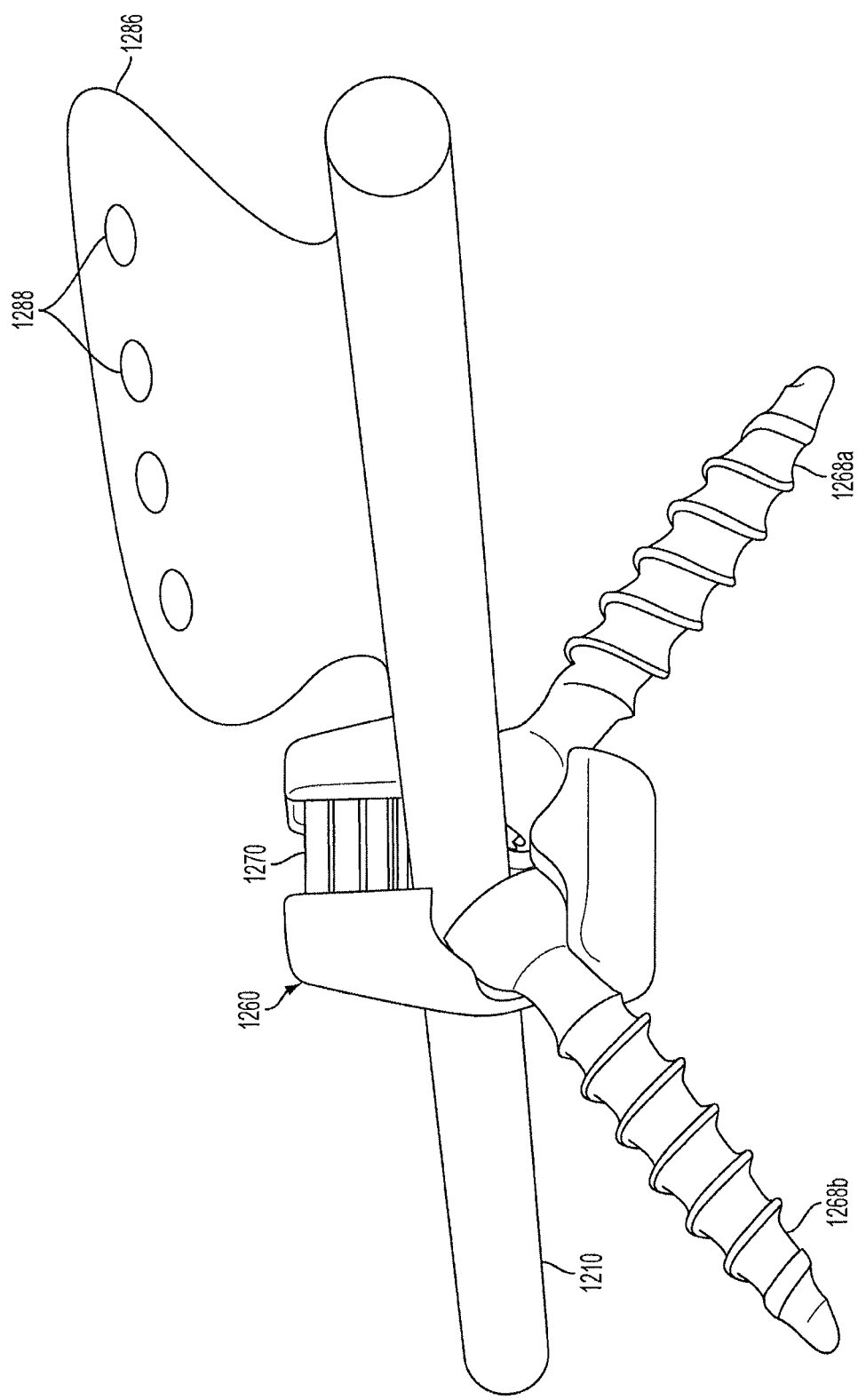
FIG. 14 is a perspective view of the housing of FIG. 12 having two anchor members disposed therein and a spinal fixation element coupled thereto.

With specific reference now to FIG. 14, an assembled spinal fixation system 1260 is shown in which a spinal fixation element 1210 is disposed within the slot 1266 of the spinal fixation assembly 1260. As discussed above, the spinal fixation element 1210 can be retained within the slot 1266 by the engagement of the set screw 1270 with internal threads 1284 formed in the arms 1264a,b. Advancement of the set screw 1270 toward the base 1272 can be effective to similarly displace the fixation element 1210 toward the base 1272. This displacement of the fixation element 1210 can force the heads 1268p of the anchor members into close engagement with the internal surfaces 1280a,b. As will be appreciated by a person skilled in the art, the engagement of the spinal fixation element 1210 with the anchor members 1268a,b can therefore help retain the anchor member 1268 within the anchor-receiving openings 978a,b.

As indicated above, spinal fixation elements can additionally include features to aid in the integration of the spinal stabilization system and promote post-surgical recovery. For example, as shown in FIG. 14, the spinal fixation element 1210 includes one or more fin(s) 1286 having a plurality of thru-holes 1288 formed therethrough. As will be appreciated by a person skilled in the art, the fin 1286 can be integral with (e.g., formed on) the spinal fixation element 1210 or can be removably coupled thereto, either before or after the spinal fixation element 1210 is seated within the slot 1266 of the spinal fixation assembly 1260. The thru-holes 1288 can provide an attachment point for muscles and other soft tissue that was previously connected to a spinous process, for example, that was resected during the spinal stabilization procedure.

The spinal fixation assemblies described above with FIGS. 9-15 can be utilized in spinal stabilization techniques. The fixation assemblies described above can be positioned within any number and/or type (e.g., cervical, thoracic, lumbar) of vertebra as required by any given procedure. Also, the method can include positioning the fixation assemblies in various manners so as to optimize the orientation of the fixation element relative to the patient's spinal column. For example, in one embodiment, the slots of the various fixation assemblies can be positioned on the midline of a patient's spine such that a single fixation element is seated and secured within the slots on the midline of the patient's spine.

Such methods can include positioning a first fixation assembly upon a first vertebra, the first fixation assembly having a proximal housing having a base and a pair of arms. The first fixation assembly can be positioned such that a slot extending between the arms and along a longitudinal axis of the first fixation assembly is aligned with a midline of the spine. An anchor member, seated in the first fixation assembly, can extend away from the housing at an acute angle relative to a central axis that is generally perpendicular to the longitudinal axis. A second fixation assembly, that is the same or different from the first, can be positioned within the second vertebra such that a slot of the second fixation assembly is aligned with the slot of the first fixation assembly. A spinal fixation element is then positioned within the slots of the first and second fixation assemblies such that the spinal fixation element extends along a midline of the spine. Finally, the spinal fixation element is secured within the slots of the first and second fixation assemblies.

As discussed above, the first and second fixation assemblies can be secured to various portions of the vertebrae. For example, during the step of positioning a first fixation assembly, the anchor member can be secured to a lamina of the first vertebra in a trans-lamina orientation. Additionally, the various portions of the target vertebrae may be modified or truncated so as to further optimize the procedure and/or provide a desired clinical outcome (e.g., decompression to alleviate pressure on the spinal cord). As discussed above, by removing portions of the target vertebra, the spinal fixation assemblies can access an optimal entry point of the vertebral bone. Further, the bone-contacting surfaces of the housing can be shaped so as to substantially correspond to the portion of bone to which the spinal assembly is implanted to improve the engagement therebetween. For example, in the vertebra 904 depicted in FIG. 11, the spinous process and one of the laminae (to the right in FIG. 11) has been removed such that the fixation assembly 960 is secured to the vertebra 904 by a single anchor 968 implanted in the remaining lamina 906 in a trans-lamina orientation. In one embodiment, the anchor member 968 is seated within the housing 962 before being secured to the lamina 906. By way of example, a driver can be inserted through the window 982 to drive the anchor member 968 into the lamina 906.

Figure 15:
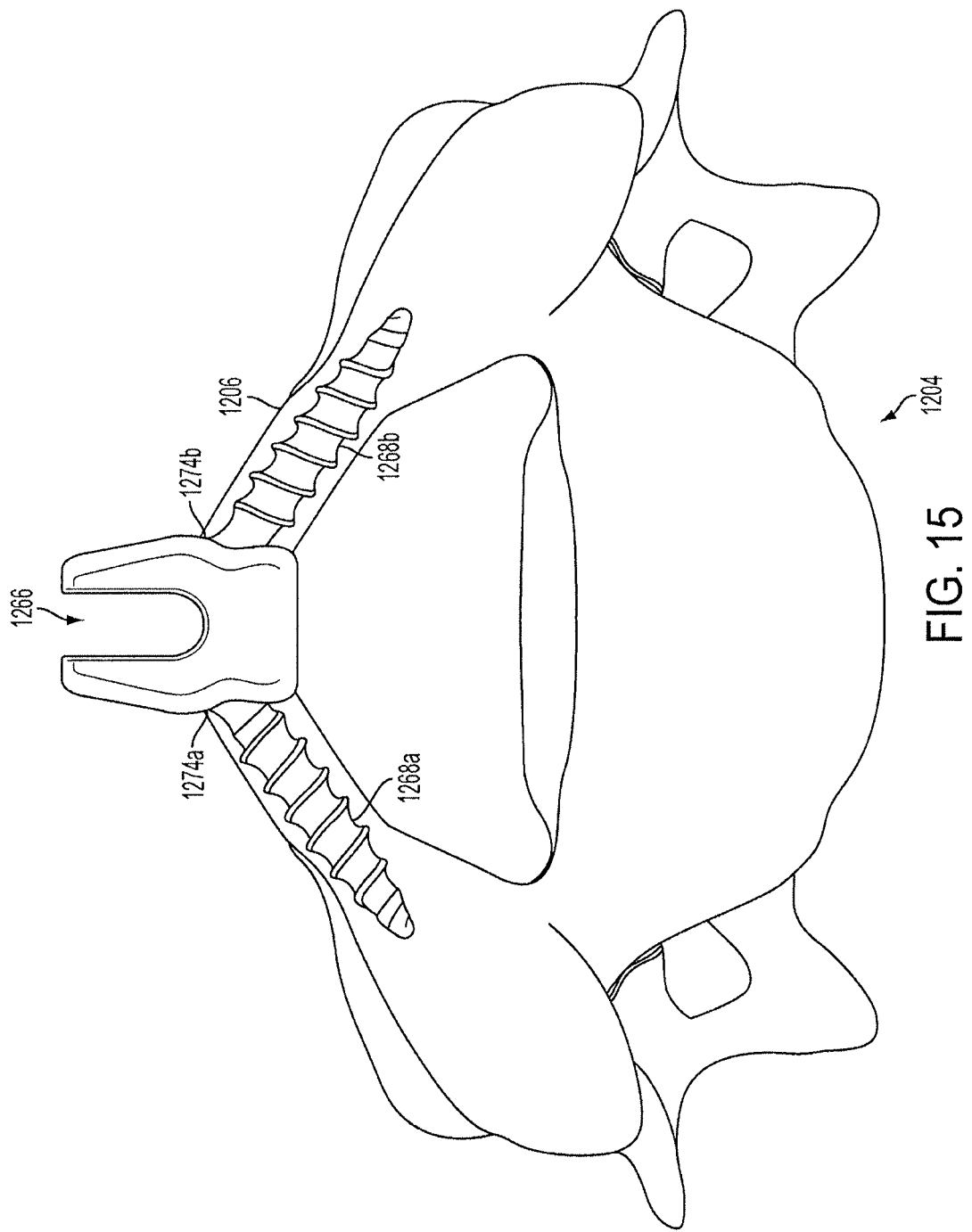
FIG. 15 is a superior view of the housing of FIG. 12 having two anchor members positioned within the lamina of a vertebra, wherein portions of the vertebra have been truncated prior to securing the assembly thereto.

With reference now to FIG. 15, a vertebra 1204 is shown in which the spinous process has been removed. The fixation assembly 1260 is secured to the laminae 1206 via two anchor members 1268 implanted within each lamina 1206 in a trans-lamina orientation. As indicated above, the anchor members 1268 can be pre-installed in the lamina and the fixation assembly 1260 can subsequently receive the heads 1268p of the anchor members 1268. For example, as shown in FIG. 14, the "open" side of the housing 1262 can be pressed in a caudal direction over the heads 1268p of the anchor members 1268 (e.g., snapped onto the heads 1268p) after the anchor members 1268 have been implanted in the laminae 1206.

One skilled in the art will appreciate further features and advantages of the presently disclosed method and system based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A method of providing spinal stabilization, comprising:
   fixing an occipital plate to the occiput of a subject with an anchor element;
   mounting a spinal fixation element upon the occipital plate such that the spinal fixation element is positioned over a midline defined by the spinal column of a subject;
   securing the spinal fixation element to the occipital plate with a floating nut such that the spinal fixation element is positioned between the occipital plate and the floating nut.

2. The method of claim 1, wherein fixing the occipital plate to the occiput comprises inserting the anchor element into the occiput through at least one opening extending through the plate.

3. The method of claim 2, wherein the anchor element is inserted into the occiput on the midline.

4. The method of claim 3, wherein the spinal fixation element is positioned over the anchor element.

5. The method of claim 2, wherein the anchor element is inserted into the occiput offset from the midline.

6. The method of claim 1, further comprising sliding the floating nut along the spinal fixation element mounted on the occipital plate to position the floating nut between the spinal fixation element and a portion of the occipital plate.

7. The method of claim 6, wherein the portion of the occipital plate is a pair of mating flanges extending from lateral edges of the occipital plate toward the midline.

8. The method of claim 1, wherein mounting the spinal fixation element upon the occipital plate includes seating the spinal fixation element in a groove formed in the occipital plate.

9. The method of claim 8, wherein fixing the occipital plate to the occiput of a subject with an anchor element includes passing the anchor element through an opening formed in the occipital plate.

10. The method of claim 1, wherein securing the spinal fixation element to the occipital plate with the floating nut includes rotating a locking element threadably disposed within a bore formed in the floating nut to bring the locking element into contact with the spinal fixation element.

11. A method of providing spinal stabilization, comprising:
    positioning an occipital plate such that a bone contacting surface thereof contacts occipital bone of a patient and extends across a midline of the patient's spine;
    implanting an anchoring device in the occipital bone such that the anchoring device is received by an opening formed in the occipital plate;
    seating a spinal fixation element against a surface of the occipital plate opposed to the bone contacting surface and between a pair of mating flanges that extend from the opposed surface;
    securing the spinal fixation element relative to the occipital plate with a floating nut having lateral projections that slidably engage the pair of mating flanges and a surface configured to seat the spinal fixation element.

12. The method of claim 11, wherein implanting an anchoring device in the occipital bone comprises implanting a plurality of anchoring devices, each of which is received within one of a plurality of openings formed in the occipital plate.

13. The method of claim 12, wherein each of the plurality of anchoring devices is implanted along the midline of the spine.

14. The method of claim 12, wherein each of the plurality of anchoring devices is implanted on one side of the midline of the spine.

15. The method of claim 11, wherein the anchoring device is implanted along the midline of the spine.

16. The method of claim 11, wherein the anchoring device is implanted on one side of the midline of the spine.

17. The method of claim 11, wherein securing the spinal fixation element relative to the occipital plate with the floating nut includes seating the spinal fixation element in a groove formed on the surface of the floating nut and translating the floating nut along the spinal fixation element relative to the occipital plate to slidably engage the lateral projections of the floating nut with the pair of mating flanges of the occipital plate.

18. The method of claim 11, further comprising rotating a locking element extending through a bore formed in the floating nut to prevent movement of the floating nut relative to the spinal fixation element and the occipital plate.

* * * * *